United States Patent
Hannah et al.

(10) Patent No.: US 6,933,306 B2
(45) Date of Patent: *Aug. 23, 2005

(54) HYDROXAMIC AND CARBOXYLIC ACID DERIVATIVES

(75) Inventors: Duncan Robert Hannah, Cambridge (GB); Hazel Joan Dyke, Cambridge (GB); Robert John Watson, Cambridge (GB); John Fraser Keily, Cambridge (GB); Andrew Douglas Baxter, Cambridge (GB)

(73) Assignee: Darwin Discovery Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/280,766

(22) Filed: Oct. 25, 2002

(65) Prior Publication Data

US 2003/0092727 A1 May 15, 2003

Related U.S. Application Data

(63) Continuation of application No. 09/855,389, filed on May 15, 2001, now Pat. No. 6,506,773.

(30) Foreign Application Priority Data

May 15, 2000 (GB) ............................................. 0011720
Mar. 23, 2001 (GB) ............................................. 0107362

(51) Int. Cl.$^7$ .................. A61K 31/4365; C07D 513/04
(52) U.S. Cl. ...................... 514/301; 546/114; 546/115; 546/113; 514/300; 514/302

(58) Field of Search ................................. 514/301, 300, 514/302, 303; 546/114, 113, 115

(56) References Cited

U.S. PATENT DOCUMENTS 6,469,020 B2 * 10/2002 Batty et al. .................. 514/290
6,734,189 B2 * 5/2004 Batty et al. .................. 514/290

FOREIGN PATENT DOCUMENTS

| EP | 0780386 | 12/1996 |
|---|---|---|
| WO | WO 9724117 | 1/1997 |
| WO | WO 9805635 | 8/1997 |
| WO | WO 9924399 | 11/1998 |
| WO | WO 0012477 | 8/1999 |
| WO | WO 0012478 | 8/1999 |

OTHER PUBLICATIONS

Orazi, O. et al. "Synthesis of Fused Heterocycles: 1, 2, 3, 4–Tetrahydroisoquinolines and Ring Homologues via Sulphonamidomethylation" *J. Chem. Soc. Perkin Trans.* 1(11):1977–1982.

* cited by examiner

*Primary Examiner*—Charanjit S. Aulakh
(74) *Attorney, Agent, or Firm*—Saliwanchik, Lloyd & Saliwanchik

(57) ABSTRACT

Pharmacologically active compounds are provided as well as pharmaceutical compositions and methods for treating cancer; inflammation; an autoimmune, infectious or ocular disease; or age-related macular degeneration in a mammal.

6 Claims, No Drawings ps
HYDROXAMIC AND CARBOXYLIC ACID DERIVATIVES

CROSS-REFERENCE TO A RELATED APPLICATION

This application is a continuation of application Ser. No. 09/855,389, filed May 15, 2001 now U.S. Pat. No. 6,506,773.

FIELD OF THE INVENTION

This invention relates to hydroxamic and carboxylic acid derivatives, and to their use in medicine.

BACKGROUND TO THE INVENTION

Metalloproteinases, including matrix metalloproteinase (MMP), collagenase, gelatinase and TNFα convertase (TACE), and their modes of action, and also inhibitors thereof and their clinical effects, are described in WO-A-96/11209, WO-A-97/12902 and WO-A-97/19075, the contents of which are incorporated herein by reference. MMP inhibitors may also be useful in the inhibition of other mammalian metalloproteinases such as the ADAM or ADAM-TS families.

Compounds which have the property of inhibiting the action of metalloproteinases involved in connective tissue breakdown, such as collagenase, stromelysin and gelatinase, have been shown to inhibit the release of TNFα both in vitro and in vivo See Gearing et al (1994), Nature 370:555–557; McGeehan et al (1994), Nature 370:558–561; GB-A-2268934, and WO-A-93/20047. All of these reported inhibitors contain a hydroxamic acid zinc-binding group, as do the imidazole-substituted compounds disclosed in WO-A-95/23790. Other compounds that inhibit MB and/or TNFα are described in WO-A-95/13289, WO-A-96/11209, WO-A-96/035687, WO-A-96/035711, WO-A-96/035712 and WO-A-96/035714.

SUMMARY OF THE INVENTION

The invention encompasses novel compounds of formula (I) which are inhibitors of matrix metalloproteinase, ADAM or ADAM-TS enzymes, and which are useful for the treatment of diseases mediated by those enzymes and/or TNFα-mediated diseases, including degenerative diseases and certain cancers.

Novel compounds according to a first aspect of the invention are represented by formula (I):

wherein $R^1$ is OH or NHOH;

$R^2$ is H, alkyl, alkenyl, alkynyl, aryl, arylalkyl, heteroaryl, heteroarylalkyl, cycloalkyl, cycloalkylalkyl, heterocyclo or heterocycloalkyl (any of which may be optionally substituted with one or more substituents selected from $R^6$, W and $WR^6$); and $R^3$ is H or alkyl;

or $R^2$, $R^3$ and the carbon atom to which they are attached together represent a carbocyclic or heterocyclic ring (either of which may be substituted with one or more substituents selected from $R^6$, W and $WR^6$);

$R^4$ is alkyl, cycloalkyl, $OR^9$, $CO_2R^{14}$, $COR^{10}$, $S(O)_qR^{10}$ where q is 0, 1 or 2, $CONR^7R^8$, CN or $S(O)_qNR^7R^8$; two $R^4$ substituents may be attached to the same carbon atom to form $C(R^4)_2$, where each $R^4$ may be the same or different, and $C(R^4)_2$ may represent C=O;

$R^5$ is alkyl, cycloalkyl, aryl, heteroaryl, heterocyclo, $CF_3$, $OR^9$, $COR^{10}$, $S(O)_qR^{10}$, $CO_2R^{14}$, $CONR^7R^8$, $S(O)_qNR^7R^8$, halogen, $NR^{10}OR^{11}$ or CN, or two adjacent $R^5$ substituents may be combined to form a heterocyclic ring;

$R^6$ is $OR^9$, $COR^{10}$, $CO_2R^{15}$, $CONR^7R^8$, $NR^{10}R^{11}$, $S(O)_qR^{10}$, $S(O)_qNR^7R^8$, =O, =$NOR^{10}$, succinimido or the group $R^7$ and $R^8$, which may be the same or different, are each H, alkyl, cycloalkyl, aryl, heteroaryl, heterocyclo, arylalkyl, heterarylalkyl, heterocycloalkyl or cycloalkylalkyl, or $R^7$ and $R^8$ and the nitrogen to which they are attached together represent a heterocyclic ring;

$R^9$ is H, alkyl, $CF_3$, $CHF_2$, $CH_2F$, cycloalkyl, aryl, heteroaryl, heterocyclo, arylalcyl, heterarylalkyl, heterocycloalkyl or cycloalkylalkyl;

$R^{10}$ is H, alkyl, cycloalkyl, aryl, heteroaryl, heterocyclo, arylalkyl, heterarylalkyl, heterocycloalkyl or cycloalkylalkyl; and $R^{11}$ is H, alkyl, cycloalkyl, aryl, heteroaryl, heterocyclo, arylalkyl, heterarylalkyl, heterocycloalkyl, cycloalkylalkyl, $COR^{12}$, $CONR^7R^8$, $S(O)_qR^{12}$ or $S(O)_qNR^7R^8$;

or $R^{10}$ and $R^{11}$ and the nitrogen to which they are attached together represent a heterocyclic ring;

$R^{12}$ is $OR^9$ or $R^{13}$;

$R^{13}$ is alkyl, cycloalkyl, aryl, heteroaryl, heterocyclo, arylalkyl, heterarylalkyl, heterocycloalkyl or cycloalkylalkyl;

$R^{14}$ is H, alkyl or cycloalkyl;

$R^{15}$ is H, alkyl or cycloalkyl, arylalkyl or heteroarylalkyl;

$R^{16}$ is H or alkyl;

A is aryl or heteroaryl, provided that when A is phenyl, $R^3$ is H;

W is alkyl, cycloalkyl, cycloalkylalkyl, aryl, arylalkyl, heteroaryl, heteroarylalkyl, heterocyclo or heterocycloalkyl;

each k and m is independently 0, 1, 2 or 3;

n is 0, 1 or 2; and p is 0, 1 or 2;

or a salt, solvate, hydrate, N-oxide, protected amino, protected carboxy or protected hydroxamic acid derivative thereof

DESCRIPTION OF THE INVENTION

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "alkyl" refers to straight or branched chain alkyl moiety having from one to six carbon atoms, including for example, methyl, ethyl, propyl, isopropyl, butyl, tert-butyl, pentyl, hexyl and the like.

The term "alkenyl" refers to a straight or branched chain alkyl moiety having two to six carbon atoms and having in addition one double bond, of either E or Z stereochemistry where applicable. The term alkenyl includes for example, vinyl, 1-propenyl, 1- and 2-butenyl, 2-methyl-2-propenyl and the like.

The term "alkynyl" refers to a straight or branched chain alkyl moiety having two to six carbon atoms and having in addition one triple bond. The term alkynyl includes for example, ethynyl, 1-propynyl, 1- and 2-butynyl, 1-methyl-2-butynyl and the like.

Cycloalkyl or carbocyclic ring refers to a non-aromatic cyclic or multicyclic, saturated or partially saturated ring system having from three to ten carbon atoms which may be optionally benzofused at any available position. Thus cycloalkyl includes, for example, cyclopropyl, cyclobutyl, cyclopentyl, cyclohexyl, cycloheptyl, cyclooctyl, tetrahydronaphthyl, bicyclo[2.2.1]heptanyl, bicyclo[2.2.1] heptenyl, cyclopentenyl, indanyl and the like.

Heterocyclo or heterocyclic ring refers to a 3 to 10 membered saturated or partially saturated monocyclic or saturated or partially saturated multicyclic hydrocarbon ring system in which one or more of the atoms in the ring system is an element other than carbon, chosen from amongst nitrogen, oxygen or sulphur (or oxidised versions thereof, such as N-oxide, sulphoxide, sulphone). Examples include azetidinyl, pyrrolidinyl, tetrahydrofuryl, piperidinyl, quinuclidinyl, tetrahydropyranyl, morpholinyl, thiomorpholinyl, piperazinyl, N-alkyl-piperazinyl, homopiperazinyl, oxazolidinyl, imidazolidinyl, thiazolidinyl, pyrazolidinyl, benzodioxole, [2,3-dihydro] benzofuryl, [3,4-dihydro]benzopyranyl, 1,2,3,4 tetrahydroquinolinyl, 1,2,3,4 tetrahydroisoquinolinyl, 8-oxabicyclo[3.2.1]octane, indolinyl, isoindolinyl, and the like.

Aryl indicates carbocyclic radicals containing 6 to 10 carbon atoms and containing either a single ring or two condensed rings. Thus aryl includes, for example, phenyl and naphthyl.

Heteroaryl refers to a 5 to 10 membered aromatic monocyclic or multicyclic hydrocarbon ring system in which one or more of the atoms in the ring system is an element other than carbon, chosen from amongst nitrogen, oxygen or sulphur (or oxidised versions thereof, such as N-oxide). In general, the heteroaryl groups may be for example monocyclic or bicyclic fused ring heteroaryl groups. Monocyclic heteroaryl groups include, for example, five- or six-membered heteroaryl groups containing one, two, three or four heteroatoms selected from oxygen, sulphur or nitrogen atoms. Bicyclic heteroaryl groups include for example eight- to ten-membered fused-ring heteroaryl groups containing one, two or more heteroatoms selected from oxygen, sulphur or nitrogen atoms.

The term heteroaryl includes, for example, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2, 3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridyl, pyridyl-N-oxide, pyrimidinyl, pyridazinyl, pyrazinyl, 1,3,5-triazinyl, 1,2,4-triazinyl, 1,2,3-triazinyl, benzofuryl, benzothienyl, benzotriazolyl, indolyl, isoindolyl, benzimidazolyl, imidazo [1,2-a]pyridyl, benzothiazolyl, benzoxazolyl, benzisoxazolyl, benzopyranyl, quinazolinyl, quinoxalinyl, naphthyridinyl, pyrido[3,4-b]pyridyl, pyrido[3,2-b]pyridyl, pyrido[4,3-b]-pyridyl, quinolinyl, isoquinolinyl, phthalazinyl, tetrazolyl and the like.

Arylalkyl includes an aryl-alkyl-group wherein the aryl and alkyl are as described herein. Heteroarylalkyl includes a heteroaryl-alkyl-group, cycloalkylalkyl includes a cycloalkyl-alkyl-group and heterocycloalkyl includes a heterocyclo-alkyl-group, wherein all groups are as defined above.

The term "halogen" includes fluorine, chlorine, bromine or iodine.

The term "benzofused" means the addition of a benzene ring sharing a common bond with the defined ring system.

The term "optionally substituted" means optionally substituted by one or more of the groups specified, at any available position or positions.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) or formula (II) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R$ where R may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Preferred compounds of the invention are those wherein any one or more of the following may apply:

One group of compounds of the invention has the formula (I) in which $R^1$ is NHOH.

In one preferred group of compounds of formula (I) $R^2$ is in particular isopropyl or isobutyl, especially isopropyl.

Another preferred group of compounds of formula (I) is where $R^2$ is a substituted alkyl group, especially substituted methyl, ethyl or propyl. $R^2$ in compounds of this type is preferably substituted by $R^6$, where $R^6$ is especially $CO_2R^{15}$, in particular $CO_2H$, $CONR^7R^8$, $NR^{10}R^{11}$, succinimido or the group

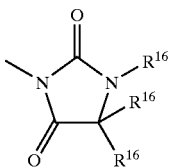

In compounds of this type $CONR^7R^8$ is in particular $CON(H)_2$, $CON(H)alkyl$, $CON(alkyl)_2$ or $R^7$ and $R^8$ are attached together to form a heterocyclic ring. $NR^{10}R^{11}$ in compounds of this type is especially $N(H)COR^{12}$ or $N(alkyl)COR^{12}$, particularly preferred is where $R^{12}$ is alkyl. Each $R^{16}$ in compounds of the invention is in particular methyl.

A further preferred group of compounds of the invention has the formula (I) where $R^2$ is an optionally substituted cycloalkyl or heterocyclo group, especially an optionally substituted heterocyclo group. In compounds of this type $R^2$ is in particular azetidinyl, pyrrolidinyl, piperidinyl, piperazinyl, tetrahydrofuryl or tetrahydropyranyl, especially optionally substituted piperidinyl. When substituted compounds of this type may in particular be substituted by $R^6$, especially where $R^6$ is $CO_2R^{15}$. $R^{15}$ may in particular be arylalkyl or heteroarylalkyl, preferably arylalkyl, especially benzyl.

$R^3$ in compounds of the invention may in particular be a hydrogen atom.

One group of compounds of the invention has the formula (I) in which $R^2$, $R^3$ and the carbon atom to which they are attached together represent an optionally substituted carbocyclic or heterocyclic ring. Especially preferred compounds in this group are those where $CR^2R^3$ is a cycloalkyl or a heterocyclic ring, in particular, $C_{3-7}$, cycloalkyl groups, especially, cyclopropyl, cyclobutyl, cyclopentyl and cyclohexyl groups, and $C_{3-7}$, heterocyclo groups, especially, azetidinyl, pyrrolidinyl, tetrahydrofuryl, tetrahydropyranyl, piperidinyl and piperazinyl. In compounds of this type $CR^2R^3$ is in particular cyclobutyl, cyclopentyl, cyclohexyl or tetrahydropyranyl.

Especially preferred is where p=1 and n=1.

In compounds of the invention k is preferably 0.

$R^5$, when present may in particular be $C_{3-7}$, cycloalkyl, aryl, monocyclic heteroaryl, $C_{3-7}$ heterocyclo, $CF_3$, $OR^9$, $CONR^7R^8$, F, Cl, Br, I or CN. Especially preferred is where $R^5$ is cyclobutyl, cyclopentyl, cyclohexyl, phenyl, $CF_3$, $OCH_3$, $OCF_3$, $OCHF_2$, $OCH_2F$, $CONH_2$, $CONHCH_3$, $CON(CH_3)_2$, CN, F, Cl, Br or I. In compounds where $R^5$ is present m is preferably 1 or 2.

One particular group of compounds of interest is represented by the formula (Ia):

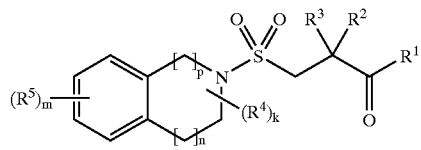

wherein $R^1$, $R^2$, $R^4$, $R^5$, k and m, n and p are as previously described. In compounds of formula (Ia) $R^3$ is a hydrogen atom.

Another group of compounds has the formula (I) wherein A is in particular pyrrolyl, furyl, thienyl, imidazolyl, oxazolyl, isoxazolyl, thiazolyl, isothiazolyl, pyrazolyl, 1,2,3-triazolyl, 1,2,3-oxadiazolyl, 1,2,5-oxadiazolyl 1,2,3-thiadiazolyl, 1,2,5-thiadiazolyl, pyridyl, pyrimidinyl, pyridazinyl, pyrazinyl, 1,2,4-triazinyl or 1,2,3-triazinyl, especially thiazolyl.

Particularly preferred compounds of the invention are:

1-[2-(3,4-Dihydro-1-H-isoquinoline-2-sulfonyl)-1-hydroxycarbamoyl-ethyl]-piperidine-1-carboxylic acid benzyl ester;

2-(6-Cyclohexyl-3,4-dihydro-1-H-isoquinoline-2-sulfonylmethyl)-N-hydroxy-3-methyl-butyramide;

N-Hydroxy-3-methyl-2-(6-phenyl-3,4-dihydro-1-H-isoquinoline-2-sulfonylmethyl)-butyramide;

2-(6,7-Dimethoxy-3,4-dihydro-1H-isoquinoline-2-sulfonylmethyl)-N-hydroxy-3-methyl-butyramide;

N-Hydroxy-3-methyl-2-(2-phenyl-6,7-dihydro-4H-thiazolo[5,4-c]pyridine-5-sulfonylmethyl)-butyramide;

and the salts, solvates, hydrates, N-oxides, protected amino, protected carboxy and protected hydroxamic acid derivatives thereof.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below, the various groups R and other variables are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience (1999).

Thus, for example, compounds of the invention may be prepared by the following general route:

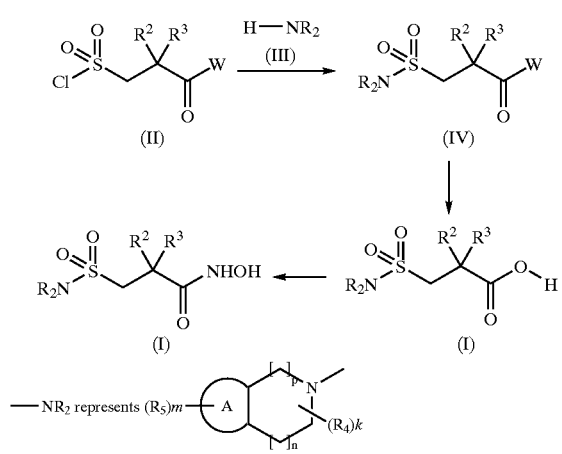

Compounds of formula (IV), where W is for example an alkoxy group, such as methoxy, ethoxy or tert-butoxy or a chiral auxiliary, for example, 4(R)-benzyl-oxazolidin-2-one, may be prepared by methods well known in the literature, for example, by reaction of a sulfonyl chloride (II) with an amine (III) in the presence of an amine base, such as triethylamine in a halogenated solvent, such as dichloromethane at room temperature.

Compounds of general formula (II) are either known or may be made by one skilled in the art using methods known in the literature, see for example WO-A-99/24399, or as described in the examples herein after. Compounds of general formula (III) are available commercially or they be made using methods known in the literature or by any method known to those skilled in the art. For example, an amine of general formula (III) may be prepared by selective hydrogenation of a heteroaryl group, such as isoquinoline using for example a platinum catalyst under acidic conditions. Appropriate conditions may be platinum (IV) oxide in the presence of concentrated hydrochloric acid in ethanol under a pressure of 690 kPa. Alternatively, an amine of formula (III) where A is a heteroaryl group such as thiazolyl or oxazolyl may be prepared by formation of such a heteroaryl group on a suitably functionalised amine ring such as N-tert-butoxycarbonyl-protected piperidin-4-one using well known methods. For example, the piperidinone (V) may be α-halogenated using standard conditions, such as reaction of the ketone with trimethylsilyl chloride and an amine base such as triethylamine in N,N-dimethylformamide at 70° C., followed by α-halogenation using, for example, N,N-bromosuccinimide in a suitable solvent such as acetonitrile. The α-bromoketone (VI) may then be reacted with a suitable amide or thioamide, such as thiobenzamide in conditions such as N,N-dimethylformamide at 80° C., to form the desired heteroaryl ring, as illustrated in the scheme below:

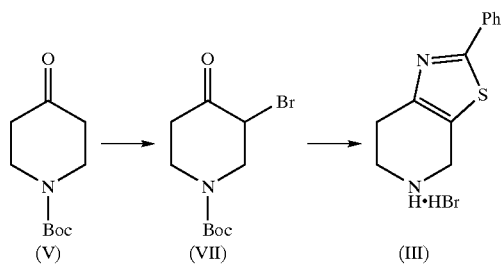

Carboxylic acids of general formula (I) may be prepared by deprotection of a suitably protected carboxylic acid of formula (IV). For example, where W is an alkoxy group, such as ethoxy, a base such as aqueous lithium hydroxide may be used, alternatively trifluoroacefic acid may be used when W is a tert-butyl group or in the case of a chiral auxiliary such as 4-(R)-benzyl-oxazolidin-2-one, lithium hydroxide/hydrogen peroxide may be used. Appropriate solvent and temperature conditions such as those described in the examples herein after may be used.

Compounds of formula (I) may also be prepared by interconversion of other compounds of formula (I). Thus, for example, hydroxamic acids of general formula (I) may be prepared using conditions well known in the literature. For example, treatment of acids of formula (I) with oxalyl chloride in an inert solvent (such as dichloromethane) gives an intermediate acid chloride, which may or may not be isolated, but which in turn is reacted with hydroxylamine at a suitable temperature such as room temperature to give the desired hydroxamic acids (I). Alternatively an acid of formula (I) maybe activated in situ using for example a diimide such as 1-(3-dimethylaminopropyl)-3-ethylcarbodiimide hydrochloride, advantageously in the presence of a catalyst such as a N-hydroxy compound, e.g. N-hydroxybenzotriazole using suitable conditions, e.g. in N,N-dimethylformamide at −15° C., prior to the subsequent addition of a suitably protected hydroxylamine such as tert-butyldimethyl silyl hydroxylamine and warming to ambient temperature. The protecting group maybe removed using appropriate conditions, such as water or tetrabutylammonium fluoride and acetic acid in tetrahydrofuran at 0° C., to yield the desired hydroxamic acids of formula (I).

Similarly, intermediates of any appropriate formula may be prepared by the interconversion of other compounds of the same formula.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysin, collagenase, gelatinase, ADAM or ADAM-TS enzymes. Compounds according to the invention may also exhibit in vitro inhibition of membrane-shedding events known to be mediated by metalloproteinases, for example, α-APP, ACE, TGF-α, TNF-α, Fas ligand, selecting, TNFR-I, TNFR-II, CD30, I1-6R, CD43, CD44, CD16-I, CD16-II, Folate receptor, CD23, or IL-1RII.

The activity and selectivity of the compounds may be determined by use of the appropriate enzyme inhibition test, for example as described in Examples A-M of WO-A-98/05635, by the assay for the inhibition of CD23 shedding described in WO-A-99/24399, or by the assay of TNF RI shedding described in WO-A-00/56704.

This invention also relates to a method of treatment for patients (including man and/or mammalian animals raised in the dairy, meat or fur industries or as pets) suffering from disorders or diseases which can be attributed to metalloproteinases.

Accordingly, the compounds of formula (I) can be used among other things in the treatment of osteoarthritis and rheumatoid artritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment or prophylaxis) of disease or conditions mediated by TNF, MMPs, ADAM or ADAM-TS enzymes, in mammals, in particular in humans, which method comprises administering to the mammal an effective, amount of a compound of formula (I) above, or a pharmaceutically acceptable salt thereof, and a compound of formula (I) for use in human or veterinary medicine, particularly in the management (by which is meant treatment or prophylaxis) of diseases or conditions mediated by TNF, MMPs, ADAM or ADAM-TS enzymes; and the use of a compound of formula (I) in the preparation of an agent for the management (by which is meant treatment or prophylaxis) of diseases or conditions mediated by TNF, MMPs, ADAM or ADAM-TS enzymes.

The disease or conditions referred to above include inflammatory diseases, autoimmune diseases, cancer, cardiovascular diseases and diseases involving tissue breakdown. Appropriate diseases include rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, bacterial infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus and solid organ transplant.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

Compounds of the invention are particularly of use in the treatment of inflammatory diseases, autoimmune diseases and cancer. Thus, for example, the compounds may be used in the treatment (including prophylaxis) of graft versus host reactions, psoriasis, atopic dermatitis, rhinitis, eczema, systemic lupus erythematosus, solid organ transplant, cystic fibrosis, rheumatoid arthritis, osteoarthritis, osteoporosis, Crohn's Disease, ulcerative colitis, multiple sclerosis, periodontitis, bone resorption, bacterial infections, epidermolysis bullosa, tumour growth, angiogenesis, ophthalmological disease, retinopathy, asthma, emphysema, bronchitis, and chronic obstructive pulmonary disease (COPD).

For the treatment of all diseases and disorders previously indicated, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. Ocular injection, such as intravitreal, subtenons, subconjunctival, periocular and retrobulbar may also be used, as well as intraocular slow release devices and implants. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108, 4,166,452 and 4,265,874, to form osmotic therapeutic tablets for controlled release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs maybe formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc, containing a compound of the invention are employed. For the purposes of this specification, topical application includes mouthwashes and gargles.

For topical ocular administration, pharmaceutically acceptable solutions, suspensions or gels containing the compounds of formula (I) may be used. Solutions and suspensions may also be adapted for intra-vitreal or intra-cameral use.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce: a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

The following abbreviations are used:

| | |
|---|---|
| Boc—tert-butoxy carbonyl; | DCM—dichloromethane |
| DMF—N,N-dimethylformamide | EtOAc—ethyl acetate |
| MeOH—methanol | NBS—N-bromosuccinimide |
| TFA—trifluoroacetic acid | |

Intermediate 1 6-Cyclohexyl-1,2,3,4-tetrahydro-isoquinoline

Platinum (IV) oxide (30 mg), then 12M hydrochloric acid (1.5 ml) was added to a solution of 6-phenyl-isoquinoline (1.52 g) in ethanol (30 ml). The mixture was transferred to a Parr high pressure apparatus and charged with hydrogen to a pressure of 50 psi. The reaction was stirred at room temperature for 3 h then recharged with hydrogen to 100 psi and left to stir for 16 h. The mixture was then filtered, fresh platinum catalyst and 12M hydrochloric acid added, and the Parr high pressure apparatus charged to 75 psi. The reaction was left to stir at room temperature for 16 h, after which a white crystalline solid was observed in the reaction mixture. Water was added to dissolve this solid and the mixture filtered through celite, washing with 1:1 water-methanol (3×30 ml). The methanol was removed under reduced pressure then the aqueous basified with concentrated sodium hydroxide solution and extracted with 2:1 diethyl ether-ethyl acetate (3×50 ml). The combined extracts were washed with water (2×20 ml), saturated sodium bicarbonate (20 ml) and brine (20 ml) then dried ($Na_2SO_4$), filtered and evaporated under reduced pressure. The residue was purified by chromatography ($SiO_2$, 93:6:1 dichloromethane-methanol-ammonia, then a second column with 94:5:1 dichloromethane-methanol-ammonia) to give the title compound (190 mg) as a mixture containing approximately 20% of a slightly higher running product.

$R_f$ 0.27 (94:5:1 dichloromethane-methanol-ammonia)

Intermediate 2 4-Benzenesulfonyloxy-piperidine-1-carboxylic acid benzyl ester

Triethylamine (17 ml) was added dropwise to a solution of benzyl 4-hydroxy-1-piperidinecarboxylate (28.83 g) in dichloromethane (100 ml) at 0° C. and stirred for 15 minutes. Benzenesulfonyl chloride (14 ml) was added and the reaction allowed to stir at room temperature for 48 h. The mixture was washed with water (50 ml), saturated sodium bicarbonate solution (50 ml), water (50 ml) and brine (50 ml) then dried (Na$_2$SO$_4$), filtered and evaporated under reduced pressure. The residue was purified by chromatography (SiO$_2$, 20% ethyl acetate in hexane to 30% ethyl acetate in hexane) to give the tide compound (31.88 g, 77%) as a white crystalline solid.

R$_f$ 0.62 (5% methanol in dichloromethane)

Intermediate 3 2-(1-Benzyloxycarbonyl-piperidin-4-yl)-malonic acid

Sodium metal (3.2 g) was dissolved in ethanol (50 ml) under a nitrogen atmosphere at room temperature. A solution of diethyl malonate (56.4 ml) in ethanol (50 ml) was added dropwise, followed by a solution of 4-benzenesulfonyloxy-piperidine-1-carboxylic acid benzyl ester (31.88 g) in ethanol (50 ml), also added dropwise. The mixture was heated to reflux for 16 h then the solvent was removed under reduced pressure. The residue was partitioned between water (100 ml) and diethyl ether (100 ml) and the aqueous washed with further diethyl ether (60 ml). The combined organics were washed with 10% citric acid solution (50 ml), water (50 ml) and brine (50 ml). After drying (Na$_2$SO$_4$) and filtering the solvent was removed under reduced pressure to leave a yellow liquid. Half of this crude diester was taken and dissolved in methanol (150 ml) and water (50 ml). Lithium hydroxide monohydrate (18.14 g) was added slowly and the reaction left to stir at room temperature for 16 h then the methanol was removed under reduced pressure. The aqueous was washed with diethyl ether (3×40 ml), acidified to pH=3 with citric acid and extracted with ethyl acetate (2×40 ml). The combined organics were washed with water (2×40 ml) and brine (40 ml), dried (Na$_2$SO$_4$), filtered and evaporated under reduced pressure to give the title compound (8.29 g, 56%) as a white crystalline solid.

R$_f$ 0.47 (5% methanol in dichloromethane)

Intermediate 4 4-(1-Carboxy-vinyl)-piperidine-1-carboxylic acid benzyl ester 2-(1-Benzyloxycarbonyl-piperidin-4-yl)-malonic acid (18.06 g) was dissolved in tetrahydrofuran (140 ml) and morpholine (4.95 ml) followed by acetic acid (6.43 ml) was added, forming a white precipitate. Formaldehyde (4.56 g) was added, causing the precipitate to disappear, and the mixture heated to reflux for 4 h. The solvent was evaporated, diethyl ether (50 ml) added and the mixture extracted with water (3×60 ml). The aqueous was acidified to pH=3 with citric acid and extracted with diethyl ether (3×30 ml). The combined organic extracts were washed with water (40 ml) and brine (40 ml), dried (Na$_2$SO$_4$), filtered and the solvent removed under reduced pressure to give the title compound (16.65 g) as a mixture containing approximately 10% of the acid starting material.

R$_f$ 0.5 (5% methanol in dichloromethane)

Intermediate 5 4-(2-Acetylsulfanyl-1-carboxy-ethyl)-piperidine-1 carboxylic acid benzyl ester 4-(1-Carboxy-vinyl)-piperidine-1-carboxylic acid benzyl ester (15.6 g) was dissolved in thioacetic acid (15 ml) and heated to reflux for 3 h. The thioacetic acid was evaporated under reduced pressure and azeotroped with 1:1 hexane-dichloromethane (4×30 ml) to give the title compound (20.32 g, 95%) as an orange oil.

R$_f$ 0.28 (40% ethyl acetate in hexane)

Intermediate 6 4-(2-Acetylsulfanyl-1-tert-butoxycarbonyl-ethyl)-piperidine-1-carboxylic acid benzyl ester Sulfuric acid (1.15 ml) was added slowly to a solution of 4-(2-acetylsulfanyl-1-carboxy-ethyl)-piperidine-1-carboxylic acid benzyl ester (20.32 g) in dichloromethane (60 ml). The mixture was cooled in an acetone/dry ice bath and cooled isobutylene (60 ml) added. The mixture was transferred to a Parr high pressure apparatus and left to stir overnight then washed with water (30 ml), saturated sodium bicarbonate solution (30 ml) and brine (30 ml). After drying (Na$_2$SO$_4$) and filtering the solvent was removed under reduced pressure and the residue purified by column chromatography (SiO$_2$, 20% ethyl acetate in hexane) to give the title compound (11.22 g, 60%) as an orange oil.

R$_f$ 0.25 (20% ethyl acetate in hexane)

Intermediate 7 4-(1-tert-Butoxycarbonyl-2-chlorosulfonyl-ethyl)-piperidine-1-carboxylic acid benzyl ester A solution of 4-(2-acetylsulfanyl-1-tert-butoxycarbonyl-ethyl)-piperidine-1-carboxylic acid benzyl ester (1.01 g) in dichloromethane (25 ml) and water (25 ml) was cooled in ice. Chlorine gas (500 mg) was bubbled through the solution over 10 minutes then the mixture was flushed with nitrogen gas. The mixture was washed with water (25 ml) and brine (25 ml), then dried (Na$_2$SO$_4$), filtered and the solvent removed under reduced pressure to give the title compound (920 mg, 86%) as a colourless oil.

R$_f$ 0.48 (30% ethyl acetate in hexane)

Intermediate 8 4-[1-tert-Butoxycarbonyl-2-(3,4-dihydro-1H-isoquinoline-2-sulfonyl)-ethyl]-piperidine-1-carboxylic acid benzyl ester 1,2,3,4-Tetrahydroisoquinoline (0.17 ml) was dissolved in dichloromethane (40 ml) at room temperature under nitrogen. Triethylamine (0.19 ml) was added, followed by 4-(1-tert-butoxycarbonyl-2-chlorosulfonyl-ethyl)-piperidine-1-carboxylic acid benzyl ester (500 mg) as a solution in dichloromethane (1.5 ml). The reaction was left to stir for 64 h then diluted with dichloromethane (60 ml), washed with 10% citric acid solution (2×50 ml), water (2×50 ml), saturated sodium bicarbonate solution (2×50 ml) and brine (50 ml). The organic layer was then dried (MgSO$_4$), filtered and the solvent removed under reduced pressure to give the title compound (506 mg, 83%) as a yellow oil.

R$_f$ 0.44 (50% ethyl acetate in heptane)

The following compounds were prepared as above.

Intermediate 9 3-Methyl-2-(6-phenyl-3-4-dihydro-1H-isoquinoline-2-sulfonylmethyl)-butyric acid tert-butyl ester From 2-chlorosulfonylmethyl-3-methyl-butyric acid tert-butyl ester (293 mg) and 6-phenyl-1,2,3,4-tetrahydro-isoquinoline (206 mg) to give, after chromatography (SiO$_2$, 25% diethyl ether in hexane), the title compound (340 mg, 78%) as a white solid.

R$_f$ 0.24 (25% diethyl ether in hexane)

Intermediate 10 2-(6-Cyclohexyl-3,4-dihydro-1H-isoquinoline-2-sulfonylmethyl)-3-methyl-butyric acid tert-butyl ester From 2-chlorosulfonylmethyl-3-methyl-butyric acid tert-butyl ester (263 mg) and 6-cyclohexyl-1,2,3,4-tetrahydro-isoquinoline (190 mg) to give, after chromatography (SiO$_2$, 25% diethyl ether in hexane), the title compound (230 mg, 58%) as a colourless gum.

R$_f$ 0.36 (25% diethyl ether in hexane)

Intermediate 11 1-tert-Butoxycarbonyl-1,2,3,6-tetrahydro-4-(trimethylsilyloxy)pyridine Trimethylsilyl chloride (25 ml) and triethylamine (50 ml) were added to a stirred solution of N-Boc piperidinone (30 g) in DMF (40 ml) and the mixture was heated at 70° C. for 16 h. The solution was cooled to room temperature and diluted with hexanes (300 ml), the solution was washed with sodium bicarbonate solution (3×100 ml), dried (MgSO$_4$) and evaporated to give a colourless oil. The product was purified on silica eluting with 10% ethyl acetate/hexanes to give the title compound as colourless oil (25 g, 62%).

R$_f$ 0.7 (20% EtOAc/hexanes)

Intermediate 12 1-tert-Butoxycarbonyl-3-bromopiperidin-4-one

NBS (1.4 g) was added to a solution of 1-tenbutoxycarbonyl-1,2,3,6-tetrahydro-4-(trimethylsilyloxy) pyridine (2 g) in acetonitrile and the mixture was stirred at room temperature for 30 minutes. The solution was diluted with ethyl acetate (50 ml) and washed with water (50 ml), sodium bicarbonate solution (50 ml) and brine (50 ml), dried ($MgSO_4$) and evaporated to give the title compound as a colourless solid (1.8 g).

$R_f$ 0.40 (20% EtOAc/hexanes)

Intermediate 13 2-Phenyl-4,5,6,7-tetrahydro-thiazolo[5,4-c] pyridine

A solution of 1-tert-butoxycarbonyl-3-bromopiperidin-4-one (8 g) and thiobenzamide (3.4 g) in DMF was heated at 70° C. for 16 h, then cooled to room temperature. The solvent was evaporated in vacuo and the residue dissolved in water (100 ml) and washed with ether (100 ml), then basified with sodium hydroxide and extracted into ethyl acetate (3×100 ml). The solvent was dried ($MgSO_4$) and evaporated to give the title compound as cream solid (2.81 g, 53% based on thiobenzamide used).

MS 217 (M+1)

EXAMPLE 1

3-Methyl-2-(6-phenyl-3,4-dihydro-1H-isoquinoline-2-sulfonylmethyl)-butyric acid

Trifluoroacetic acid (5 ml) was added to a solution of 3-methyl-2-(6-phenyl-3-4-dihydro-1H-isoquinoline-2-sulfonylmethyl)-butyric acid tert-butyl ester (0.33 g) in dichloromethane (20 ml). The reaction was stirred at room temperature for 4 h then evaporated under reduced pressure. Diethyl ether (10 ml) was added to the residue then extracted with 1M sodium hydroxide solution. The aqueous was extracted with diethyl ether (10 ml), acidified with citric acid to pH=3 then extracted with ethyl acetate (3×10 ml). The combined ethyl acetate extracts were washed with water (2×10 ml) and brine (10 ml), dried ($Na_2SO_4$), filtered and evaporated under reduced pressure to give the title compound (250 mg, 87%) as a white solid.

$R_f$ 0.26 (50% diethyl ether in hexane plus acetic acid)

MS 388 (M+1), 386 (M−1)

The following compound was prepared as above.

EXAMPLE 2

2-(6-Cyclohexyl-3,4-dihydro-1H-isoquinoline-2-sulfonylmethyl)-3-methyl-butyric acid From 2-(6-cyclohexyl-3,4-dihydro-1H-isoquinoline-2-sulfonylmethyl)-3-methyl-butyric acid tert-butyl ester (230 mg) to give the title compound (164 mg, 82%) as a white solid.

$R_f$ 0.27 (50% diethyl ether in hexane plus acetic acid)

MS 394 (M+1), 392 (M−1)

EXAMPLE 3

2-(6,7-Dimethoxy-3,4-dihydro-1H-isoquinoline-2-sulfonylmethyl)-3-methyl-butyric acid 2-Chlorosulfonylmethyl-3-methyl-butyric acid tert-butyl ester (1.0 ml of a 1M solution in dichloromethane) was added to a solution of 6,7-dimethoxy-1,2,3,4-tetrahydroisoquinoline hydrochloride (230 mg) and triethylamine (0.31 ml) in dichloromethane (10 ml) and the mixture stirred at room temperature for 16 h. Trifluoroacetic acid was added (5 ml) and the reaction left to stir for 2 h then diluted with hexane (10 ml) and evaporated under reduced pressure. The residue was azeotroped with 1:1 dichloromethane-hexane (2×10 ml), dissolved in 1M sodium hydroxide and washed with diethyl ether (2×10 ml) The aqueous was acidified to pH=4 with citric acid and extracted with ethyl acetate (2×15 ml). The combined extracts were washed with water (10 ml) and brine (10 ml), dried ($Na_2SO_4$), filtered and evaporated under reduced pressure to give the title compound (93 mg, 25%).

$R_f$ 0.43 (5% methanol in dichloromethane)

MS (M+1) 372 and (M−1) 370

EXAMPLE 4

3-Methyl-2-(2-phenyl-6,7-dihydro-4H-thiazolo[5,4-c]pyridine-5-sulfonylmethyl)-butyric acid 2-Phenyl-4,5,6,7-tetrahydro-thiazolo[5,4-c]pyridine (0.11 g) was added to a solution of 2-chlorosulfonylmethyl-3-methyl-butyric acid tert-butyl ester (0.14 g) and triethylamine (0.3 ml) in DCM (20 ml) at room temperature. The solution was stirred for 2 h, then TFA (5 ml) was added and the mixture stirred for 1 h. The mixture was evaporated in vacuo and the residue partitioned between diethyl ether (10 ml) and saturated sodium bicarbonate (30 ml). The aqueous layer was acidified with citric acid to pH 5 and extracted with ethyl acetate (3×20 ml). The solvent was dried ($MgSO_4$) and evaporated to give the title compound as pale yellow solid (0.15 g).

$R_f$ 0.32 (EtOAc)

EXAMPLE 5

1-[2(3,4-Dihydro-1H-isoquinoline-2-sulfonyl)-1-hydroxycarbamoyl-ethyl]-piperidine-1-carboxylic acid benzyl ester Trifluoroacetic acid (5.0 ml) was added to a solution of 4-[1-tert-butoxycarbonyl-2-(3,4-dihydro-1H-isoquinoline-2-sulfonyl)ethyl]-piperidine-1-carboxylic acid benzyl ester (506 mg) in dichloromethane (30 ml). The reaction was stirred at room temperature for 3.5 h then the solvent and excess trifluoroacetic acid evaporated under reduced pressure to give the carboxylic acid as a yellow solid. This was dissolved in dichloromethane (30 ml) under a nitrogen atmosphere and oxalyl chloride (0.1 ml) added, followed by N,N-dimethylformamide (a few drops, catalytic). The reaction was left to stir for 16 h then evaporated under reduced pressure to give the acid chloride as a yellow solid. This was suspended in tetrahydrafuran (10 ml) and 50%wt solution of aqueous hydroxylamine (0.30 ml) was added. The reaction was left to stir at room temperature for 20 minutes then the solvent was evaporated under reduced pressure. The residue was triturated with water (20 ml), the resulting solid filtered off and washed with water (10 ml). Purification by reverse phase preparative HPLC using a 25 cm×21.4 mm Phenomenex Luna C18 (2) (5 u) column and a mobile phase of aqueous trifluoroacetic acid (0.05% v/v) and acetonitrile under gradient conditions from 20% to 70% acetonitrile gave the title compound (83 mg, 18%) as a pale yellow solid, >98% pure by HPLC analysis.

$R_f$ 0.18 (5% methanol in dichloromethane)

MS 500 (M−1)

EXAMPLE 6

2-(6-Cyclohexyl-3,4-dihydro-1H-isoquinoline-2-sulfonylmethyl)-N-hydroxy-3-methyl-butyramide 2-(6-Cyclohexyl-3,4-dihydro-1H-isoquinoline-2-sulfonylmethyl)-3-methyl-butyric acid (143 mg) was dissolved in dichloromethane (15 ml) under a nitrogen atmosphere and oxalyl chloride (0.15 ml) added, followed by a solution of 10% N,N-dimethylformamide in dichloromethane (7 drops). The reaction was stirred at room temperature for 2 h then evaporated under reduced pressure and azeotroped with 1:1 dichloromethane-hexane (2×10 ml). The residue was dried under vacuum then suspended in tetrahydrofuran (15 ml) and treated with 50% wt solution of aqueous hydroxylamine (0.7 ml). The mixture was left to stir at room temperature for 1 h then evaporated under reduced pressure. The residue was triturated with water (20 ml) and the resulting solid filtered off, washed with water (10 ml) and dried under vacuum at 40° C. to give the title compound (120 mg, 82%).

$R_f$ 0.32 (5% methanol in dichloromethane)

MS 407 (M−1)

The following compounds were prepared as above.

EXAMPLE 7

N-Hydroxy-3-methyl-2-(6-phenyl-3,4-dihydro-1H-isoquinoine-2-sulfonylmethyl)-butyramide From 3-methyl-2-(6-phenyl-3,4-dihydro-1H-isoquinoline-2-sulfonylmethyl)-butyric acid (230 mg), to give the title compound (220 mg, 93%).

$R_f$ 0.28 (5% methanol in dichloromethane)

MS 403 (M+1)

EXAMPLE 8

2(6,7-Dimethoxy-3,4-dihydro-1H-isoquinoline-2-sulfonylmethyl)-N-hydroxy-3-methyl-butyramide From 2-(6,7-dimethoxy-3,4-dihydro-1H-isoquinoline-2-sulfonylmethyl)-3-methyl-butyric acid (80 mg), to give the title compound (71 mg, 85%).

$R_f$ 0.27 (5% methanol in dichloromethane)

MS 387 (M+1)

EXAMPLE 9

N-Hydroxy-3-methyl-2-(2-phenyl-6,7-dihydro-4H-thiazolo[5,4-c]pyridine-5-sulfonylmethyl)-butyramide From 3-methyl-2-(2-phenyl-6,7-dihydro-4H-thiazolo[5,4-c]pyridine-5 sulfonyl methyl)-butyric acid (0.15 g), to give the title compound as beige solid (85 mg).

$R_f$ 0.33 (7% MEOH/DCM)

MS 409 (M+1)

We claim:

1. A compound of formula (I)

wherein $R^1$ is OH or NHOH;

$R^2$ is H, alkyl, alkenyl, alkynyl, aryl, arylalkyl, heteroaryl, heteroarylalkyl, cycloalkyl, cycloalkylalkyl, heterocyclo or heterocycloalkyl (any of which may be optionally substituted with one or more substituents selected from $R^6$, W and $WR^6$); and $R^3$ is H or alkyl;

or $R^2$, $R^3$ and the carbon atom to which they are attached together represent a carbocyclic or heterocyclic ring (either of which may be substituted with one or more substituents selected from $R^6$, W and $WR^6$);

$R^4$ is alkyl, cycloalkyl, $OR^9$, $CO_2R^{14}$, $COR^{10}$, $S(O)_qR^{10}$ where q is 0, 1 or 2, $CONR^7R^8$, CN or $S(O)_qNR^7R^8$; two $R^4$ substituents may be attached to the same carbon atom to form $C(R^4)_2$, where each $R^4$ may be the same or different, and $C(R^4)_2$ may represent C=O; $R^5$ is alkyl, cycloalkyl, aryl, heteroaryl, heterocyclo, $CF_3$, $OR^9$, $COR^{10}$, $S(O)_qR^{10}$, $CO_2R^{14}$, $CONR^7R^8$, $S(O)_qNR^7R^8$, halogen, $NR^{10}OR^{11}$ or CN, or two adjacent $R^5$ substituents may be combined to form a heterocyclic ring;

$R^6$ is $OR^9$, $COR^{10}$, $CO_2R^{15}$, $CONR^7R^8$, $NR^{10}R^{11}$, $S(O)_qR^{10}$, $S(O)_qNR^7R^8$, =O, =$NOR^{10}$, succinimido or the group $R^7$ and $R^8$, which may be the same or different, are each H, alkyl, cycloalkyl, aryl, heteroaryl, heterocyclo, arylalkyl, heterarylalkyl, heterocycloalkyl or cycloalkylalkyl, or $R^7$ and $R^8$ and the nitrogen to which they are attached together represent a heterocyclic ring;

$R^9$ is H, alkyl, $CF_3$, $CHF_2$, $CH_2F$, cycloalkyl, aryl, heteroaryl, heterocyclo, arylalkyl, heterarylalkyl, heterocycloalkyl or cycloalkylalkyl;

$R^{10}$ is H, alkyl, cycloalkyl, aryl, heteroaryl, heterocyclo, arylalkyl, heterarylalkyl, heterocycloalkyl or cycloalkylalkyl; and $R^{11}$ is H, alkyl, cycloalkyl, aryl, heteroaryl, heterocyclo, arylalkyl, heterarylalkyl, heterocycloalkyl, cycloalkylalkyl, $COR^{12}$, $CONR^7R^8$, $S(O)_qR^{12}$ or $S(O)_qNR^7R^8$;

or $R^{10}$ and $R^{11}$ and the nitrogen to which they are attached together represent a heterocyclic ring;

$R^{12}$ is $OR^9$ or $R^{13}$;

$R^{13}$ is alkyl, cycloalkyl, aryl, heteroaryl, heterocyclo, arylalkyl, heterarylalkyl, heterocycloalkyl or cycloalkylalkyl;

$R^{14}$ is H, alkyl or cycloalkyl;

$R^{15}$ is H, alkyl or cycloalkyl, arylalkyl or heteroarylalkyl;

$R^{16}$ is H or alkyl;

A is heteroaryl;

W is alkyl, cycloalkyl, cycloalkylalkyl, aryl, arylalkyl, heteroaryl, heteroarylalkyl, heterocyclo or heterocycloalkyl;

each k and m is independently 0, 1, 2 or 3;

n is 0 or 1;

p is 0, 1 or 2; and p+n=2 or a salt, solvate, hydrate, N-oxide, protected amino, protected carboxy or protected hydroxamic acid derivative thereof.

2. The compound of claim 1, wherein $R^1$ is NHOH.

3. The compound of claim 1, which is selected from 3-methyl-2-(2-phenyl-6,7-dihydro-4H-thiazolo[5,4-c]pyridine-5-sulfonylmethyl)-butyric acid, N-hydroxy-3-methyl-2-(2-phenyl-6,7-dihydro-4H-thiazolo[5,4-c]pyridine-5-sulfonylmethyl)butyramide.

4. A pharmaceutical composition, comprising a compound of formula (I)

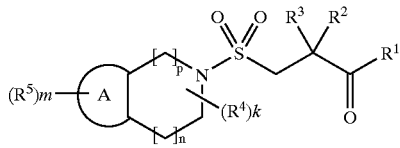

wherein
$R^1$ is OH or NHOH;
$R^2$ is H, alkyl, alkenyl, alkynyl, aryl, arylalkyl, heteroaryl, heteroarylalkyl, cycloalkyl, cycloalkylalkyl, heterocyclo or heterocycloalkyl (any of which may be optionally substituted with one or more substituents selected from $R^6$, W and $WR^6$); and
$R^3$ is H or alkyl;
or $R^2$, $R^3$ and the carbon atom to which they are attached together represent a carbocyclic or heterocyclic ring (either of which may be substituted with one or more substituents selected from $R^6$, W and $WR^6$);
$R^4$ is alkyl, cycloalkyl, $OR^9$, $CO_2R^{14}$, $COR^{10}$, $S(O)_qR^{10}$ where q is 0, 1 or 2, $CONR^7R^8$, CN or $S(O)_qNR^7R^8$; two $R^4$ substituents may be attached to the same carbon atom to form $C(R^4)_2$, where each $R^4$ may be the same or different, and $C(R^4)_2$ may represent C=O; $R^5$ is alkyl, cycloalkyl, aryl, heteroaryl, heterocyclo, $CF_3$, $OR^9$, $COR^{10}$, $S(O)_qR^{10}$, $CO_2R^{14}$, $CONR^7R^8$, $S(O)_qNR^7R^8$, halogen, $NR^{10}R^{11}$ or CN, or two adjacent $R^5$ substituents may be combined to form a heterocyclic ring;
$R^6$ is $OR^9$, $COR^{10}$, $CO_2R^{15}$, $CONR^7R^8$, $NR^{10}OR^{11}$, $S(O)_qR^{10}$, $S(O)_qNR^7R^8$, =O, =$NOR^{10}$, succinimido or the group

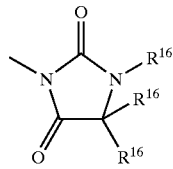

$R^7$ and $R^8$, which may be the same or different, are each H, alkyl, cycloalkyl, aryl, heteroaryl, heterocyclo, arylalkyl, heterarylalkyl, heterocycloalkyl or cycloalkylalkyl, or $R^7$ and $R^8$ and the nitrogen to which they are attached together represent a heterocyclic ring;
$R^9$ is H, alkyl, $CF_3$, $CHF_2$, $CH_2F$, cycloalkyl, aryl, heteroaryl, heterocyclo, arylalkyl, heterarylalkyl, heterocycloalkyl or cycloalkylalkyl;
$R^{10}$ is H, alkyl, cycloalkyl, aryl, heteroaryl, heterocyclo, arylalkyl, heterarylalkyl, heterocycloalkyl or cycloalkylalkyl; and
$R^{11}$ is H, alkyl, cycloalkyl, aryl, heteroaryl, heterocyclo, arylalkyl, heterarylalkyl, heterocycloalkyl, cycloalkylalkyl, $COR^{12}$, $CONR^7R^8$, $S(O)_qR^{12}$ or $S(O)_qNR^7R^8$;
or $R^{10}$ and $R^{11}$ and the nitrogen to which they are attached together represent a heterocyclic ring;
$R^{12}$ is $OR^9$ or $R^{13}$;
$R^{13}$ is alkyl, cycloalkyl, aryl, heteroaryl, heterocyclo, arylalkyl, heterarylalkyl, heterocycloalkyl or cycloalkylalkyl;
$R^{14}$ is H, alkyl or cycloalkyl;
$R^{15}$ is H, alkyl or cycloalkyl, arylalkyl or heteroarylalkyl;
$R^{16}$ is H or alkyl;
A is heteroaryl; W is alkyl, cycloalkyl, cycloalkylalkyl, aryl, arylalkyl, heteroaryl, heteroarylalkyl, heterocyclo or heterocycloalkyl;
each k and m is independently 0, 1, 2 or 3;
n is 0 or 1;
p is 0, 1 or 2; and p+n=2
or a salt, solvate, hydrate, N-oxide, protected amino, protected carboxy or protected hydroxamic acid derivative thereof;
and a pharmaceutically-acceptable diluent or carrier.

5. The pharmaceutical composition, according to claim 4, wherein $R^1$ is NHOH.

6. The pharmaceutical composition, according to claim 4, wherein said compound is selected from
3-methyl-2-(2-phenyl-6,7-dihydro-4H-thiazolo[5,4-c]pyridine-5-sulfonylmethyl)-butyric acid,
N-hydroxy-3-methyl-2-(2-phenyl-6,7-dihydro-4H-thiazolo[5,4-c]pyridine-5-sulfonylmethyl)butyramide.

* * * * *

UNITED STATES PATENT AND TRADEMARK OFFICE
CERTIFICATE OF CORRECTION

PATENT NO. : 6,933,306 B2
APPLICATION NO. : 10/280766
DATED : August 23, 2005
INVENTOR(S) : Hannah et al.

It is certified that error appears in the above-identified patent and that said Letters Patent is hereby corrected as shown below:

Column 18,
Line 13, "$NR^{10}OR^{11}$" should read --$NR^{10}R^{11}$--.
Line 67, "-butyric acid," should read --butyric acid, and--.

Column 19,
Line 35, "$NR^{10}OR^{11}$" should read --$NR^{10}R^{11}$--.

Column 20,
Line 44, "-butyric acid," should read --butyric acid, and--.

Signed and Sealed this

Fifth Day of December, 2006

JON W. DUDAS
*Director of the United States Patent and Trademark Office*